US00PP22700P2

(12) United States Plant Patent
Dekker

(10) Patent No.: US PP22,700 P2
(45) Date of Patent: May 1, 2012

(54) ***CHRYSANTHEMUM* PLANT NAMED 'DEKMAKI'**

(50) Latin Name: *Chrysanthemum×morifolium*
Varietal Denomination: Dekmaki

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 190 days.

(21) Appl. No.: 12/799,433

(22) Filed: Apr. 23, 2010

(51) Int. Cl.
*A01H 5/00* (2006.01)

(52) U.S. Cl. ..... Plt./294

(58) Field of Classification Search ..... Plt./294
See application file for complete search history.

(56) References Cited

OTHER PUBLICATIONS

UPOV ROM GTITM Computer Database GTI Jouve Retrieval Software 2011/10 Citation for 'Dekmaki'.*

* cited by examiner

*Primary Examiner* — Wendy C Haas
(74) *Attorney, Agent, or Firm* — C. A. Whealy

(57) ABSTRACT

A new and distinct cultivar of *Chrysanthemum* plant named 'Dekmaki', characterized by its daisy-type inflorescences with white-colored quilled ray florets; strong and upright flowering stems; early, freely and uniform flowering habit; and good postproduction longevity

2 Drawing Sheets

Botanical designation: *Chrysanthemum×morifolium.*
Cultivar denomination: 'DEKMAKI'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Dekmaki'.

The new *Chrysanthemum* plant is a product of a planned breeding program conducted by the Inventor in Hensbroek, The Netherlands. The objective of the breeding program is to create new daisy-type *Chrysanthemum* plants with large inflorescences, strong flowering stems, early flowering response, attractive ray floret coloration and shape and excellent postproduction longevity.

The new *Chrysanthemum* plant originated from a cross-pollination made by the Inventor in Hensbroek, The Netherlands on Feb. 22, 2007, of a proprietary selection of *Chrysanthemum×morifolium* identified as code number 04.42081.03, not patented, as the female, or seed, parent with a proprietary selection of *Chrysanthemum×morifolium* identified as code number 05.39833.03, not patented. The new *Chrysanthemum* plant was discovered and selected by the Inventor as a single flowering plant from within the progeny of the stated cross-pollination in a controlled greenhouse environment in Hensbroek, The Netherlands in October, 2007.

Asexual reproduction of the new *Chrysanthemum* plant by terminal cuttings in a controlled greenhouse environment in Hensbroek, The Netherlands since November, 2007, has shown that the unique features of this new *Chrysanthemum* plant are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dekmaki'. These characteristics in combination distinguish 'Dekmaki' as a new and distinct *Chrysanthemum* plant:

1. Daisy-type inflorescences with white-colored quilled ray florets.
2. Strong and upright flowering stems.
3. Early, freely and uniform flowering habit.
4. Good postproduction longevity; plants maintain good substance for about 23 days in an interior environment.

Plants of the new *Chrysanthemum* differ from plants of the female parent selection in the following characteristics:

1. Plants of the new *Chrysanthemum* have larger leaves than plants of the female parent selection.
2. Plants of the new *Chrysanthemum* flower three days earlier than plants of the female parent selection.
3. Plants of the new *Chrysanthemum* have larger inflorescences than plants of the female parent selection.
4. Plants of the new *Chrysanthemum* and the female parent selection differ in ray floret color as plants of the female parent selection have pink-colored ray florets.

Plants of the new *Chrysanthemum* differ from plants of the male parent selection in the following characteristics:

1. Plants of the new *Chrysanthemum* have smaller leaves than plants of the male parent selection.
2. Plants of the new *Chrysanthemum* flower 19 days earlier than plants of the male parent selection.
3. Plants of the new *Chrysanthemum* have smaller inflorescences than plants of the male parent selection.
4. Plants of the new *Chrysanthemum* and the male parent selection differ in ray floret color as plants of the male parent selection have yellow-colored ray florets.

Plants of the new *Chrysanthemum* can be compared to plants of *Chrysanthemum×morifolium* 'Dekallwhite', not patented. In side-by-side comparisons conducted in Hensbroek, The Netherlands, plants of the new *Chrysanthemum* differed from plants of 'Dekallwhite' in the following characteristics:

1. Plants of the new *Chrysanthemum* flowered five days earlier than plants of 'Dekallwhite'.
2. Plants of the new *Chrysanthemum* had smaller inflorescences than plants of 'Dekallwhite'.
3. Ray florets of plants of the new *Chrysanthemum* were quilled in shape whereas ray florets of plants of 'Dekallwhite' were ligulate in shape.

BRIEF DESCRIPTION OF THE PHOTOGRAPHS

The accompanying colored photographs illustrate the overall appearance of the new *Chrysanthemum* plant. These photographs show the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'Dekmaki' grown as a spray-type.

The photograph on the second sheet comprises close-up views of the upper (top of photograph) and lower surfaces (bottom of photograph) of typical inflorescences and leaves of 'Dekmaki'.

DETAILED BOTANICAL DESCRIPTION

The aforementioned photographs and following observations and measurements describe plants grown during the winter in Hensbroek, The Netherlands, under commercial practice in ground beds in a glass-covered greenhouse. Plants were initially given 1.5 weeks of long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants were 6.5 weeks old when the photographs and the description were taken. In the following description, color references are made to The Royal Horticultural Society Colour Chart, 2007 Edition, except where general terms of ordinary dictionary significance are used.

Botanical classification: *Chrysanthemum×morifolium* 'Dekmaki'.

Parentage:

*Female, or seed, parent.*—Proprietary selection of *Chrysanthemum×morifolium* identified as code number 04.42081.03, not patented.

*Male, or pollen, parent.*—Proprietary selection of *Chrysanthemum×morifolium* identified as code number 05.39833.03, not patented.

Propagation:

*Type.*—Terminal vegetative cuttings.

*Time to initiate roots, summer.*—About four days at 20° C.

*Time to initiate roots, winter.*—About six days at 20° C.

*Time to produce a rooted young plant, summer.*—About 13 days at 20° C.

*Time to produce a rooted young plant, winter.*—About 15 days at 20° C.

*Root description.*—Fine, fibrous; light brown in color.

*Rooting habit.*—Freely branching, moderately dense.

Plant description:

*Appearance/growth habit.*—Herbaceous daisy-type cut flower that is typically grown as a spray-type; moderately vigorous growth habit.

*Flowering stem description.*—Aspect: Erect. Strength: Strong. Length: About 60 cm. Stem diameter: About 4 mm. Spray diameter: About 18 cm. Internode length: About 1 cm to 2 cm. Texture: Finely pubescent; longitudinally ridged. Color: Close to 146C.

*Foliage description.*—Arrangement: Alternate; simple. Length: About 4.5 cm to 8.5 cm. Width: About 3 cm to 4.5 cm. Apex: Cuspidate. Base: Attenuate. Margin: Palmately lobed, serrate; sinuses parallel to divergent. Texture, upper and lower surfaces: Pubescent, slightly rough; veins prominent on lower surface. Venation pattern: Pinnate, reticulate. Color: Developing leaves, upper surface: Close to 137B. Developing leaves, lower surface: Close to 147B. Fully developed leaves, upper surface: Close to N137C; venation, close to 146B to 146C. Fully developed leaves, lower surface: Close to 147B; venation, close to 146C. Petiole: Length: About 1 cm to 1.5 cm. Diameter: About 3 mm to 4 mm. Texture, upper and lower surfaces: Slightly rough. Color, upper surface: Close to 146B to 146C. Color, lower surface: Close to 146C.

Inflorescence description:

*Appearance.*—Daisy-type inflorescence form with quilled-shaped ray florets and tubular disc florets; inflorescences borne perpendicular to axillary laterals (peduncles); ray and disc florets develop acropetally on a capitulum.

*Fragrance.*—Moderately fragrant.

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering response; plants exposed to 1.5 weeks of long day/short night conditions after planting followed by photoinductive short day/long night conditions flower about 35 days later when grown as a spray-type.

*Postproduction longevity.*—In an interior environment, inflorescences and foliage will maintain good color and substance for about 23 days; inflorescences persistent.

*Quantity of inflorescences.*—Grown as a spray type, about 30 inflorescences develop.

*Inflorescence size.*—Diameter: About 3 cm. Depth (height): About 1 cm. Disc diameter: About 8 mm. Receptacle height: About 3 mm. Receptacle diameter: About 4 mm. Receptacle color: Close to 145A.

*Inflorescence buds.*—Shape: Flattened spherical. Height: About 3 mm. Diameter: About 5 mm. Color: Close to 137C.

*Ray florets.*—Length: About 1.1 cm to 1.7 cm. Width: About 1 cm to 2 cm. Shape: Quilled. Apex: Emarginate. Base: Fused. Margin: Not applicable. Texture, upper and lower surfaces: Smooth, glabrous; satiny. Number per inflorescence: About 60 arranged in about three whorls. Aspect: About 10° to 30° from horizontal. Color: When opening and fully opened, upper surface: Close to NN155D. When opening and fully opened, lower surface: Close to NN155D.

*Disc florets.*—Shape: Fused tubular, erect and elongated. Apex: Dentate. Length: About 2 mm to 3 mm. Diameter: About 0.5 mm. Number per inflorescence: About 175, massed at the center of the receptacle. Color: When opening: Apex: Close to 145A. Mid-section: Close to 12B. Base: Close to 145D. Fully opened: Apex: Close to 11A. Mid-section: Close to 12C. Base: Close to 145D.

*Involucral bracts.*—Length: About 4 mm to 8 mm. Width: About 2 mm to 4 mm. Shape: Oval-shaped. Apex: Rounded. Base: Rounded to truncate. Margin Entire. Texture, upper and lower surfaces: Smooth, glabrous. Number per inflorescence: About 25 arranged in about two to three whorls. Color, upper and lower surfaces: Close to N137A.

*Peduncles.*—Length, terminal peduncle: About 8 cm. Length, fourth peduncle: About 8 cm. Length, seventh peduncle: About 9 cm to 11 cm. Diameter: About 1.5 mm to 2 mm. Strength: Moderately strong. Angle: About 30° from the flowering stem axis. Texture: Pubescent. Color: Close to 146B.

*Reproductive organs.*—Androecium: Not observed. Gynoecium: Not observed.

*Seed/fruit.*—Seed and fruit production have not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Dekmaki' as illustrated and described.

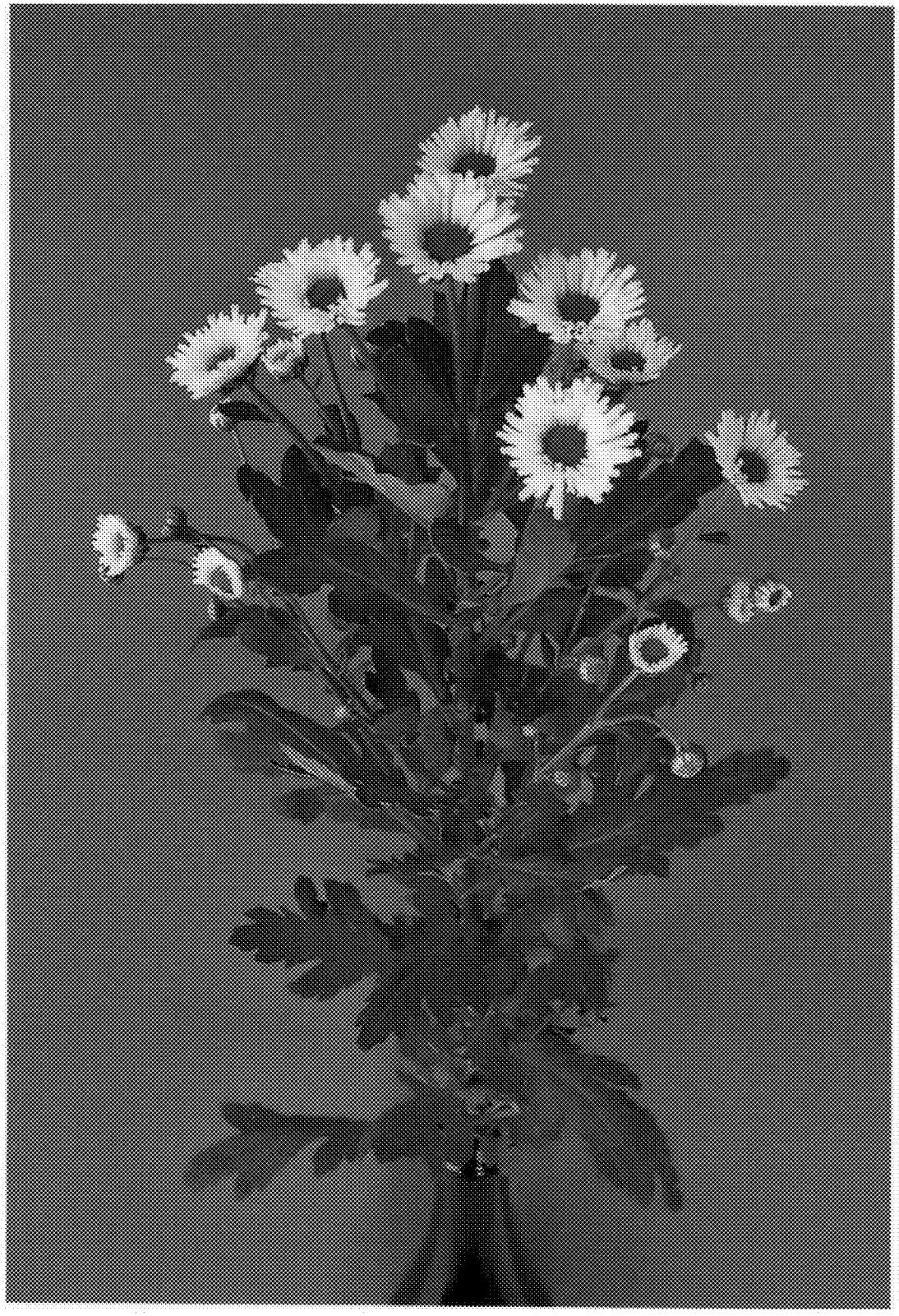

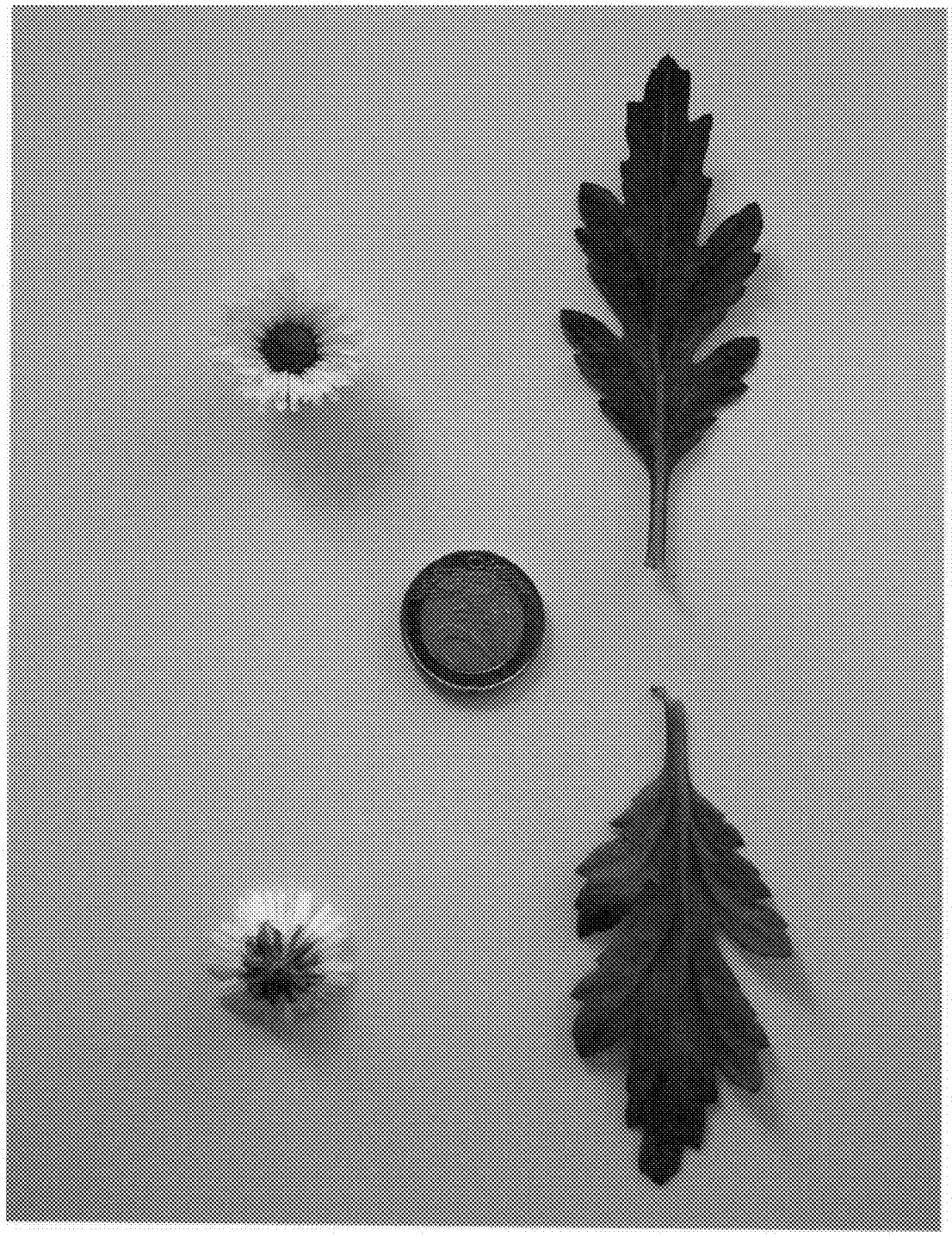

* * * * *